US009074174B2

(12) United States Patent
Kim (10) Patent No.: US 9,074,174 B2
(45) Date of Patent: Jul. 7, 2015

(54) COMPOSITE OF ENZYME AND CARBON STRUCTURE COMPLEX, METHOD FOR PRODUCING THE SAME AND USE THEREOF

(75) Inventor: Jungbae Kim, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 31 days.

(21) Appl. No.: 13/698,743

(22) PCT Filed: May 11, 2011

(86) PCT No.: PCT/KR2011/003455
§ 371 (c)(1),
(2), (4) Date: Feb. 4, 2013

(87) PCT Pub. No.: WO2011/145826
PCT Pub. Date: Nov. 24, 2011

(65) Prior Publication Data
US 2013/0143130 A1 Jun. 6, 2013

(30) Foreign Application Priority Data

May 20, 2010 (KR) .................. 10-2010-0047338

(51) Int. Cl.
*H01M 8/16* (2006.01)
*C12N 9/04* (2006.01)
*C12Q 1/00* (2006.01)
*C12N 11/02* (2006.01)

(52) U.S. Cl.
CPC .............. *C12N 9/0006* (2013.01); *C12Q 1/001* (2013.01); *C12Q 1/006* (2013.01); *C12N 11/02* (2013.01); *H01M 8/16* (2013.01); *Y02E 60/527* (2013.01)

(58) Field of Classification Search
None
See application file for complete search history.

(56) References Cited

U.S. PATENT DOCUMENTS

| 5,641,539 A * | 6/1997 | Afeyan et al. .................. 427/222 |
| 8,642,308 B1 * | 2/2014 | Atanassov et al. ............. 435/181 |
| 2007/0077483 A1 * | 4/2007 | Kubo et al. ..................... 429/43 |

(Continued)

FOREIGN PATENT DOCUMENTS

| KR | 10 2009 0004674 | 1/2009 |
| WO | WO-2010/005548 | 1/2010 |

OTHER PUBLICATIONS

International Search Report for Application No. PCT/KR2011/003455; dated Feb. 6, 2012.

*Primary Examiner* — Patrick Ryan
*Assistant Examiner* — Jose Colucci Rios
(74) *Attorney, Agent, or Firm* — Novick, Kim & Lee, PLLC; Jae Youn Kim (57) ABSTRACT

Disclosed is a composite of enzyme and carbon structure. In the composite of enzyme and carbon structure, a significantly large amount of an enzymeis immobilized on the surface of carbon structures without the formation of chemical bonds (particularly, covalent bonds) between the enzyme molecules and the carbon structures. Since the surface of the carbon structures does not need to be modified to form chemical bonds, the electrical conductivity of the composite of enzyme and carbon structure is not reduced and the stability of the composite is maintained high even after the passage of a long time in various environments. Therefore, the use of the composite of enzyme and carbon structure enables the fabrication of various devices, such as biosensors and biofuel cells, with markedly improved performance as compared to the use of conventional enzyme/carbon structure composites.

14 Claims, 7 Drawing Sheets

(56) References Cited

U.S. PATENT DOCUMENTS

2008/0014471 A1* 1/2008 Kim .................................. 429/2
2009/0008248 A1  1/2009 Shimomura et al.
2009/0198117 A1  8/2009 Cooper et al.

* cited by examiner

COMPOSITE OF ENZYME AND CARBON STRUCTURE COMPLEX, METHOD FOR PRODUCING THE SAME AND USE THEREOF

CROSS-REFERENCE TO RELATED APPLICATION

This application is a national stage application filed under 35 U.S.C. 371 of International Application No. PCT/KR2011/003455, filed May 11, 2011, which claims priority from Korean Patent Application No. 10-2010-0047338, filed May 20, 2010, each of which is incorporated by reference herein in its entirety.

TECHNICAL FIELD

The present invention relates to a composite of enzyme and carbon structure, a method for producing the same, and use thereof. More specifically, the present invention relates to a composite of enzyme and carbon structure, in which a significantly large amount of an enzyme is immobilized on elongated carbon structures without the formation of covalent bonds between the enzyme and the carbon structures, and the immobilized enzyme can be maintained stable for a long period of time, as compared to conventional composite of enzyme and carbon structure. The present invention also relates to a method for producing the composite, and use of the composite in biosensors, biofuel cells, enzyme columns, enzyme-linked immunosorbent assay (ELISA) kits, bioremediation devices, antifouling agents, and ibuprofen production.

BACKGROUND ART

Enzyme/carbon structure composites can be used in a wide variety of applications, such as biosensors, biofuel cells, enzyme columns, ELISA kits, bioremediation devices, antifouling agents, and ibuprofen production, according to their purpose of use. In these applications, the carbon structures have various shapes, for example, carbon nanotubes, carbon nanorods and carbon nanowires.

Figure 1:
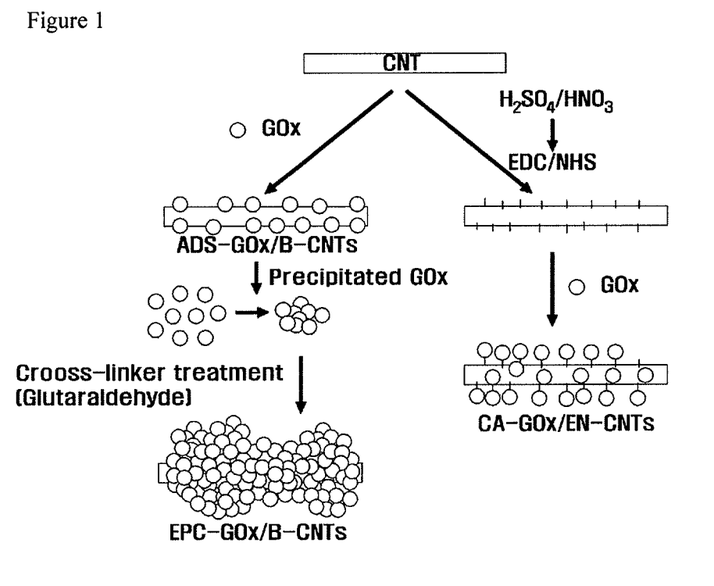
FIG. 1 is a schematic diagram showing a method for producing a composite of enzyme and carbon nanotube structure according to a preferred embodiment of the present invention (left), and a method for producing a composite of enzyme and carbon structure according to the prior art.

For the use of a conventional enzyme/carbon structure composite, for example, in a fuel cell electrode or a biosensor, an enzyme should be immobilized on the surface of carbon structures. Due to the absence of functional groups capable of chemically bonding to the enzyme on the surface of the carbon structures, covalent bonds are formed between the enzyme and the carbon structures by modifying the surface of the carbon structures, followed by post-processing to produce the enzyme/carbon structure composite. Specifically, the right hand side of FIG. 1 shows a method for producing the conventional enzyme/carbon structure (e.g., carbon nanotube) composite. As shown in FIG. 1, the surface of the carbon structures is oxidized by treatment with a strong acid to form reactive groups capable of covalently bonding to the enzyme thereon. Thereafter, the surface-modified carbon structures are treated with a linker, such as EDC/NHS, and the enzyme is added to form covalent bonds between the carbon structures and the enzymes.

A larger amount of the enzyme can be immobilized on the surface of the carbon structures when covalent bonds are formed therebetween than when the enzyme is simply adsorbed onto the carbon structures. In addition, the formation of covalent bonds ensures relatively high stability and efficiency. However, the surface modification of the carbon structures for the formation of covalent bonds leads to a marked reduction in the electrical conductivity of the carbon structures. Further, the enzyme/carbon structure composite fails to achieve noticeable stability for successful application to enzyme fuel cells and biosensors, such as glucose sensors, that require repeated long-term use in various environments. The reason for this failure is known to be because the enzyme immobilized by only one or two covalent bonds is prone to denaturation over a long time or under rigorous conditions.

DISCLOSURE

Technical Problem

The present invention has been made in an effort to solve the above problems, and it is a first object of the present invention to provide a method for stably immobilizing a significantly large amount of an enzyme on the surface of elongated carbon structures.

It is a second object of the present invention to provide a composite of enzyme and carbon structure, in which a significantly large amount of an enzyme can be immobilized stable on the surface of carbon structures despite the substantial absence of functional groups capable of covalently bonding to the enzyme on the surface of the carbon structures.

Technical Solution

In order to achieve the first object of the present invention, there is provided a method for producing a composite of enzyme and carbon structure, including (1) adsorbing enzyme molecules onto surfaces of elongated carbon structures, (2) adding a precipitant to the mixture of enzyme molecules and carbon structures to precipitate the adsorbed enzymes, and (3) adding a cross-linker to the resulting structures to cross-link the precipitated enzyme molecules.

In a preferred embodiment of the present invention, the carbon structures may have a diameter in the micrometer or nanometer range and may be, for example, carbon nanotubes, carbon rods or carbon wires.

In a further preferred embodiment of the present invention, the surfaces of the carbon structures may be unmodified.

In another preferred embodiment of the present invention, the precipitant may be selected from aqueous solutions of methanol, ethanol, 1-propanol, 2-propanol, butyl alcohol, acetone, polyethylene glycol (PEG), ammonium sulfate, sodium chloride, sodium sulfate, sodium phosphate, potassium chloride, potassium sulfate and potassium phosphate, and mixtures thereof; and the precipitant may have a concentration of 10 to 50% by weight.

In another preferred embodiment of the present invention, the cross-linker may include one or more compounds selected from the group consisting of diisocyanates, dianhydrides, diepoxides, dialdehydes, diimides, 1-ethyl-3-dimethylaminopropylcarbodiimide, glutaraldehyde, bis(imido esters), bis (succinimidyl ester), and diacid chlorides.

In another preferred embodiment of the present invention, the enzyme molecules may form shells surrounding the carbon structures without the formation of covalent bonds between the enzyme and the carbon structures.

In another preferred embodiment of the present invention, the enzyme may be selected from the group consisting of chymotrypsin, trypsin, subtilisin, papain, lipase, horse radish peroxidase, soybean peroxidase, chloroperoxidase, manganese peroxidase, tyrosinase, laccase, cellulase, xylanase, lactase, sucrase, organophosphohydrolase, cholin esterase, glucose oxidase, alcohol dehydrogenase, glucose dehydrogenase, hydrogenase, glucose isomerase, and mixtures thereof.

In order to achieve the second object of the present invention, there is provided a composite of enzyme and carbon structure including: elongated carbon structures; and shells including an enzyme surrounding the carbon structures, wherein no covalent bonds are formed between the enzyme and the carbon structures.

In a preferred embodiment of the present invention, the carbon structures may be selected from carbon nanotubes, carbon nanorods, and carbon nanowires.

In a further preferred embodiment of the present invention, the surfaces of the carbon structures may be unmodified.

In another preferred embodiment of the present invention, the shells may have a thickness of 10 to 1,000 nm.

According to another preferred embodiment of the present invention, there is provided a device selected from the group consisting of biosensors, biofuel cells, enzyme columns, ELISA kits, bioremediation devices, antifouling agents, and ibuprofen production, wherein the device includes the composite of enzyme and carbon structure.

Advantageous Effects

In comparison with conventional composites in which enzymes are covalently bonded to surface-modified carbon structures, the composite of enzyme and carbon structure of the present invention includes a significantly large amount of an enzyme immobilized on carbon structures. In addition, the immobilized enzymes are prevented from escaping from the composite of enzyme and carbon structure of the present invention when an external impact is applied to the composite. Therefore, the stability of the composite according to the present invention can be maintained even after the passage of a long period of time.

The surface of the carbon structures may not need to be modified to form functional groups participating in the formation of covalent bonds with the enzymes. Even in this case, a large amount of the enzyme can be stably immobilized on the surface of the carbon structures.

Therefore, the use of the composite of enzyme and carbon structure according to the present invention enables the fabrication of biosensors, biofuel cells, enzyme columns, ELISA kits, bioremediation devices, antifouling agents, and ibuprofen production with markedly improved performance as compared to the use of conventional enzyme/carbon structure composites.

DESCRIPTION OF DRAWINGS

FIG. 4a shows polarization curves of a biofuel cell employing EPC-GOx/B-CNTs and a biofuel cell employing CA-GOx/EN-CNTs, and FIG. 4b graphically shows power-current curves of the biofuel cells;

BEST MODE

The present invention will now be described in more detail.

As described above, the conventional methods for immobilizing enzymes on carbon structures have disadvantages of very low yield and poor long-term stability. Due to these disadvantages, the conventional methods are extremely difficult to commercialize. Further, a sufficient amount of the enzymes is not immobilized on the unmodified surface of the carbon structures, making the methods commercially nonviable. The surface modification of the carbon structures by treatment with a strong acid can improve the immobilization rate of the enzymes, but in many cases the electrical conductivity of the carbon structures is lowered and the stability of the immobilized enzymes deteriorates after the passage of a long time.

In an effort to find a solution to the above problems, the present invention provides a method for producing a composite of enzyme and carbon structure, including (1) adsorbing an enzyme onto surfaces of elongated carbon structures, (2) adding a precipitant to the enzyme-adsorbed carbon structures to precipitate the adsorbed enzyme, and (3) adding a cross-linker to the resulting structures to cross-link the precipitated enzyme molecules. In comparison with conventional composites, a composite of enzyme and carbon structure produced by the method of the present invention includes a significantly large amount of an enzyme immobilized on the surface of carbon structures. In addition, the immobilized enzymes are prevented from escaping from the composite of enzyme and carbon structure when an external impact is applied to the composite. Therefore, the stability of the composite of enzyme and carbon structure can be maintained even after the passage of a long period of time. The surface of the carbon structures may not need to be modified to form functional groups participating in the formation of covalent bonds with the enzyme. Even in this case, a large amount of the enzymes can be stably immobilized on the surface of the carbon structures.

First, in step (1), enzymes are adsorbed onto the surface of elongated carbon structures. The diameter of the carbon structures may be in the micrometer or nanometer range. The carbon structures are not limited to a particular shape so long as they extend in the lengthwise direction. Preferably, the carbon structures are carbon nanotubes, carbon nanorods, or carbon nanowires. Carbon nanotubes are more preferred.

The surface of the carbon structures may be modified before addition of the enzyme. In this case, the carbon structures include functional groups capable of covalently bonding to the enzyme. Alternatively, the surface of the carbon structures may remain unmodified. In this case, no functional groups are formed. It is preferred to leave the surface of the carbon structures unmodified, which is very advantageous because the electrical conductivity of the carbon structures is not reduced. In a preferred embodiment of the present invention, there is no need to carry out a surface modification process, such as oxidation, for the formation of covalent bonds between the carbon structures and the enzyme prior to step (1). According to this embodiment, no chemical bonds (particularly, covalent bonds) between the carbon structures and the enzyme are artificially formed.

The surface modification process, such as oxidation, for the formation of functional groups on the surface of the carbon structures essentially brings about a reduction in the electrical conductivity of the carbon structures. When it is intended to electrochemically apply the enzyme immobilized on the surface-modified carbon structure, the reduced electrical conductivity of the surface-modified carbon structures gives negative results. It takes about 1 to 3 days to modify the surface of the carbon structures. Therefore, elimination of the surface modification process simplifies the overall production procedure.

There is no restriction as to the kind of the enzyme. For example, any enzyme that can be adsorbed onto the surface of the carbon structures according to the intended purpose of use may be used in the present invention. Examples of preferred enzymes suitable for use in the present invention include, but are not limited to, chymotrypsin, trypsin, subtilisin, papain, lipase, horseradish peroxidase, soybean peroxidase, chloroperoxidase, manganese peroxidase, tyrosinase, laccase, cellulase, xylanase, lactase, sucrase, organophosphohydrolase, cholin esterase, glucose oxidase, alcohol dehydrogenase, glucose dehydrogenase, hydrogenase, and glucose isomerase. These enzymes may be used alone or as a mixture thereof.

There is no restriction as to the method for adsorbing the enzyme onto the surface of the carbon structures, such as carbon nanotubes. The enzyme can be adsorbed onto the surface of the carbon structures by various methods known in the art, for example, by dipping the carbon structures in a solution containing the enzyme.

Next, in step (2), a precipitant is added to the enzyme-adsorbed carbon structures to precipitate the adsorbed enzyme.

The enzyme adsorbed onto the surface of the carbon structures is too small to be substantially observed with the naked eye. The addition of the precipitant causes the adsorbed enzyme molecules to aggregate. As the aggregates of the enzyme molecules grow, the enzyme molecules are precipitated on the surface of the carbon structures. Any precipitant that can precipitate the enzyme without substantially affecting the activity of the enzyme may be used without limitation in the present invention. The precipitant is preferably selected from aqueous solutions of methanol, ethanol, 1-propanol, 2-propanol, butyl alcohol, acetone, PEG, ammonium sulfate, sodium chloride, sodium sulfate, sodium phosphate, potassium chloride, potassium sulfate and potassium phosphate, and mixtures thereof.

Next, in step (3), a cross-linker is added to cross-link the precipitated enzyme molecules. As a result of the cross-linking, aggregates of the enzyme molecules are formed. The enzyme aggregates and each of the carbon structures form a corn dog shape consisting of a sausage (corresponding to the carbon structure) and rising dough (corresponding to the cross-linked enzyme) surrounding the sausage. That is, the enzyme aggregates are coated on the outer surface of the carbon structure. In the preferred case where the surface of the carbon structures remains unmodified, no artificial chemical bonds (covalent bonds) between the carbon structures and the enzyme are formed. That is, the enzyme aggregates form shells surrounding the carbon structures and no covalent bonds are created between the carbon structures and the enzyme aggregates.

In the method of the present invention, the enzyme-adsorbed carbon structures may be directly treated with the cross-linker without using the precipitant. In this case, the surface of the carbon structures is not substantially coated with the enzyme.

Further, the amount of the enzyme molecules gathering around the surface of the carbon structures is not sufficient to form cross-linking bonds, making efficient coating with the enzyme impossible. According to this approach, it was confirmed that the activity of the enzyme is similar to that of a covalently bonded enzyme and the stability of the enzyme remains far below the level required in the present invention.

Any cross-linker that does not inhibit the activity of the enzyme and can cross-link the enzyme molecules may be used without limitation in the present invention. The cross-linker is preferably selected from the group consisting of diisocyanates, dianhydrides, diepoxides, dialdehydes, diimides, 1-ethyl-3-dimethylaminopropylcarbodiimide, glutaraldehyde, bis(imido esters), bis(succinimidyl ester), diacid chlorides, and mixtures thereof. Glutaraldehyde is more preferred. However, it will be obvious to those skilled in the art that any cross-linker known in the art may be used without limitation.

Preferably, the shells consist of several to several hundred layers of the enzyme molecules. The shells may have a thickness of 10 to 1,000 nm, more preferably 15 to 300 nm.

After step (3), the composite of enzyme and carbon structure may be washed with aqueous solution to remove the added cross-linker and precipitant.

According to a preferred embodiment, the present invention provides a composite of enzyme and carbon structure including: elongated carbon structures; and shells including an enzyme surrounding the carbon structures, wherein no covalent bonds are formed between the enzymes and the carbon structures.

Figure 5A:
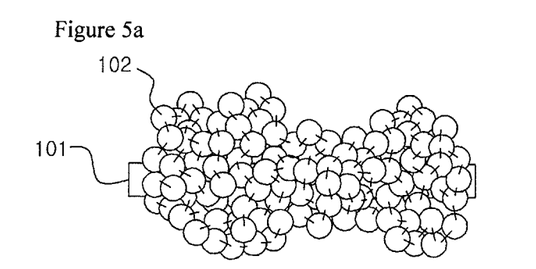
FIGS. 5a and 5b are perspective and cross-sectional diagrams showing a composite of enzyme and carbon structure according to a preferred embodiment of the present invention, respectively.
Figure 5B:
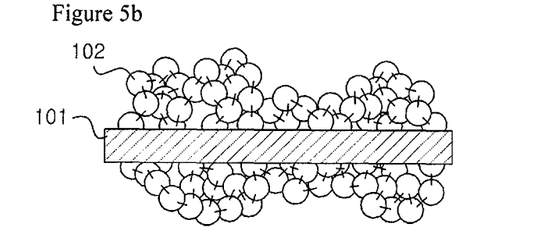

FIGS. 5a and 5b are perspective and cross-sectional diagrams showing a composite of enzyme and carbon structure according to a preferred embodiment of the present invention, respectively. As shown in FIGS. 5a and 5b, shells including enzyme aggregates surround the surface of carbon structures. FIG. 5b cross-sectionally shows a portion of the composite of enzyme and carbon structure in which the shell (102) including enzyme aggregates surrounds the surface of the carbon structure (101), like a corn dog. No covalent bonds are formed between the carbon structure, such as a carbon nanotube, and the enzymes. The shell-forming enzyme aggregates form multi-layers of the enzyme molecules rather than a monolayer. The enzyme molecules are cross-linked to each other in the enzyme aggregates. Even though the bonding strength between the carbon structure and the enzyme is relatively weak due to the absence of covalent bonds therebetween, the formation of the shell consisting of multi-layers of the enzyme molecules bonded to each other prevents the enzyme molecules from denaturation or escaping. As a consequence, a significantly large amount of the enzyme can be immobilized and the amount of the enzyme immobilized is not very much reduced even after the passage of a long time as compared to in conventional covalently bonded composites. The solid lines in FIGS. 5a and 5b indicate cross-linking bonds between the enzyme molecules.

To conclude, in the composite of enzyme and carbon structure of the present invention, the enzyme molecules precipitated on the surface of the carbon structures are cross-linked to form shells surrounding the surface of the carbon structures, thus eliminating the need to modify the surface of the carbon structure, for example, with a strong acid, to create functional groups capable of covalently bonding to the enzyme. Therefore, even in the case where no covalent bonds are formed between the carbon structures and the enzymes, a large amount of the enzyme forms shells in which the enzyme molecules are cross-linked to each other and can be immobilized on the surface of the carbon structures, like corn dogs. The formation of the shells without the surface modification of the carbon structures can prevent a reduction in the electrical conductivity of the carbon structures, which may arise when the carbon structures are modified, and can maintain the activity of the enzyme even after the passage of a long time because the carbon structures are not simply bonded to the enzyme by several covalent bonds therebetween.

As is apparent from the foregoing, in comparison with conventional composites, the composite of enzyme and carbon structure of the present invention includes a significantly large amount of the enzyme immobilized on the carbon structures. In addition, the immobilized enzyme can be maintained stable for a long period of time.

Furthermore, there is no need to modify the surface of the carbon structures, for example, with a strong acid, which prevents the physical properties of the carbon structure from deteriorating.

Accordingly, the use of the composite of enzyme and carbon structure according to the present invention enables the fabrication of biosensors, biofuel cells, enzyme columns, ELISA kits, bioremediation devices, antifouling agents, and ibuprofen production with markedly improved performance as compared to the use of conventional enzyme/carbon structure composites.

MODE FOR INVENTION

The present invention will be explained in detail with reference to the following examples.

EXAMPLE 1

Preparation of Glucose Oxidase (GOx) Precipitated on Bare CNTs (Carbon Nanotubes Whose Surface was not Modified with Strong Acid, Etc.)

Bare CNTs (2 mg, multi-walled, 30±15 nm in outer diameter and 1-5 μm in length, purity>95%, Nanolab, Inc., Newton, Mass., USA) were mixed with 1 ml of a 10 mg/ml GOx solution. The mixture of the bare CNTs (B-CNTs) and the GOx was stirred at 100 rpm and room temperature for 1 hr. For better adsorption of the GOx onto the bare CNTs, the mixture was left standing at 4° C. for 12 hr to produce ADS-GOx/B-CNTs ("simple adsorption").

1 ml of a 22 wt % ammonium sulfate solution as a precipitant was added to 1 ml of a 10 mg/ml GOx solution and stirred at room temperature for 30 min. After the GOx solution treated with the 22 wt % ammonium sulfate solution was mixed with 2 mg of ADS-GthdB-CNTs in 3 ml of PB buffer, a 0.25% glutaraldehyde (GA) solution as a cross-linker was added thereto to produce EPC-GOx/B-CNTs. Then, the resulting solution was stirred at 100 rpm and room temperature for 30 min and stored at 4° C. for 12 hr.

CNTs were treated with 2 mg of EDC-NHS in a 100 mM MES buffer. 1 ml of a 10 mg/ml GOx solution was mixed with the CNTs surface modified by treatment with 2 mg of EDC-NHS in 3 ml of PB buffer, followed by stirring at 100 rpm and room temperature for 1 hr to produce CA-GOx/EN-CNTs. The mixture was left standing at 4° C. for 12 hr for sufficient reaction. All samples were washed several times with a 100 mM PB buffer to prevent the enzyme from leaking any more. The washed samples were stored at 4° C. before use.

EXAMPLE 2

Preparation of Enzymeanode

Carbon paper (CP) (Fuel Cell Store, San Diego, Calif., USA) having a thickness of 370 μm and an area of 0.332 $cm^2$ was used as a material for an enzyme anode for the operation of a biofuel cell. The CP was hydrophilized with a solution of sulfuric acid and nitric acid (3:1). The acid-treated CP was dipped in a 0.5% Nafion solution of each sample for 10 min to prepare an enzyme anode. Thereafter, the enzyme anode was removed from the Nafion solution, dried for 1 hr, washed several times with a 100 mM PB buffer, and stored at 4° C.

EXAMPLE 3

Measurement of Power of Biofuel Cell

A PEM type small-sized biofuel cell of 3.5 cm×3 cm was fabricated using the enzyme anode. The performance of the biofuel cell was measured using a Bio-Logic SP-150 (TN, USA). The biofuel cell essentially included the enzyme anode including the carbon paper, an anode chamber, a current collector, and a membrane (MEA). A cation exchange membrane, an air pump, and a Pt cathode were purchased from Fuel Cell Store (San Diego, Calif., USA). A 200 mM glucose solution as a fuel was prepared using 100 mM PB and placed in the anode chamber. A sufficient amount of air was supplied to the cathode. The polarization curve of the biofuel cell was plotted by using the mode of constant load discharge (CLD).

The electrochemical performance of ADS-GOx/B-CNTs in which GOx was precipitated and coated on the surface of CNTs dissolved in water without acid treatment was compared with that of CA-GOx/EN-CNTs in which the enzyme was covalently bonded to CNTs treated with EDC-NHS.

FIG. 1 schematically shows a method for producing EPC-GOx/B-CNTs (cross-linked after addition of the precipitant) and a method for producing CA-GOx/EN-CNTs (covalently bonded after surface modification). According to the former method, ammonium sulfate was added to ADS-GOx/B-CNTs (simply adsorbed) to precipitate GOx, and GA was added to crosslink the precipitated GOx molecules to form GOx aggregates, which were coated on the surface of the CNTs. According to the latter method, CA-GOx/EN-CNTs was produced by reaction of EDC-NHS-treated CNTs with a GOx solution to form covalent bonds between the GOx and the CNTs.

Figure 2:
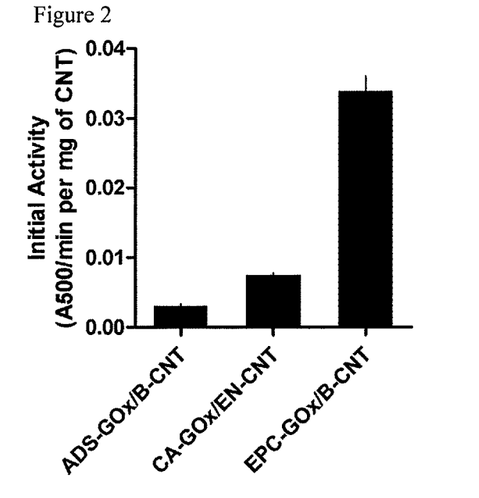
FIG. 2 graphically shows the activities of ADS-GOx/B-CNTs (enzyme-adsorbed), EPC-GOx/B-CNTs (composite according to an embodiment of the present invention), and CA-GOx/EN-CNTs (enzyme covalently bonded after surface modification)

FIG. 2 graphically shows the activities of ADS-GOx/B-CNTs (enzyme-adsorbed), EPC-GOx/B-CNTs (composite according to an embodiment of the present invention), and CA-GOx/EDC-NHS-CNTs (enzyme covalently bonded after surface modification). The initial activities of ADS-GOx/B-CNTs, EPC-GOx/B-CNTs and CA-GOx/EN-CNTs were 0.003, 0.034 and 0.0074 A500/min, respectively (FIG. 2). The activity of EPC-GOx/B-CNTs was about 10 times higher than that of ADS-GOx/B-CNTs and about 5 times higher than that of CA-GOx/EN-CNTs. The higher activity of EPC-GOx/B-CNTs can be explained by the increased enzyme loading. The enzyme precipitation plays a role in increasing the loading of EPC-GOxper unit weight of CNTs and the activity of the enzyme.

Figure 3:
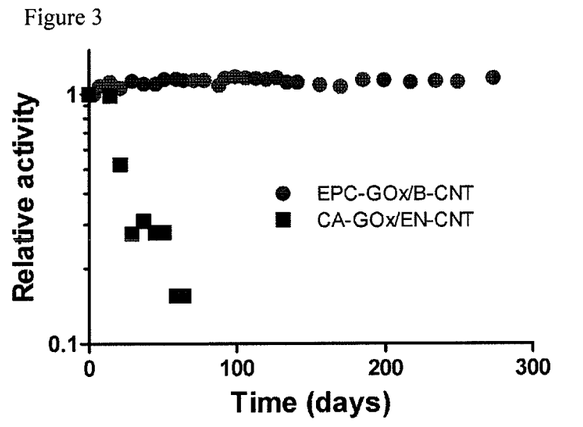
FIG. 3 graphically shows changes in the stability of EPC-GOx/B-CNTs and CA-GOx/EN-CNTs over time.

FIG. 3 graphically shows changes in the stability of EPC-GOx/B-CNTs and CA-GOx/EN-CNTs over time. The active sites of the composites were determined by the analysis of GOx from the composites taken portionwise from main stacks, all of which had been stored at room temperature. For about 270 days, EPC-GOx/B-CNTs lost almost no their activity while the activity of CA-GOx/EN-CNTs was continuously reduced. The activity of EPC-GOx/B-CNTs at 50° C. was much better than the activities of the composites produced by the other GOx immobilization methods. These results indicate that the enzyme molecules bonded in several layers were prevented from denaturation and leaking from EPC-GOx/B-CNTs despite weak bonding between the CNTs and the GOx. The shape of EPC-GOx/B-CNTs was observed by SEM. The SEM image of EPC-GOx/B-CNTs shows that several layers of the enzyme molecules were coated on the B-CNTs to form shells tightly surrounding the B-CNTs. The shells protected the enzyme from leakage for a long time. From these results, it can be expected that EPC-GOx/B-CNTs will show better electrochemical performance than CA-GOx/EN-CNTs.

Figure 4:
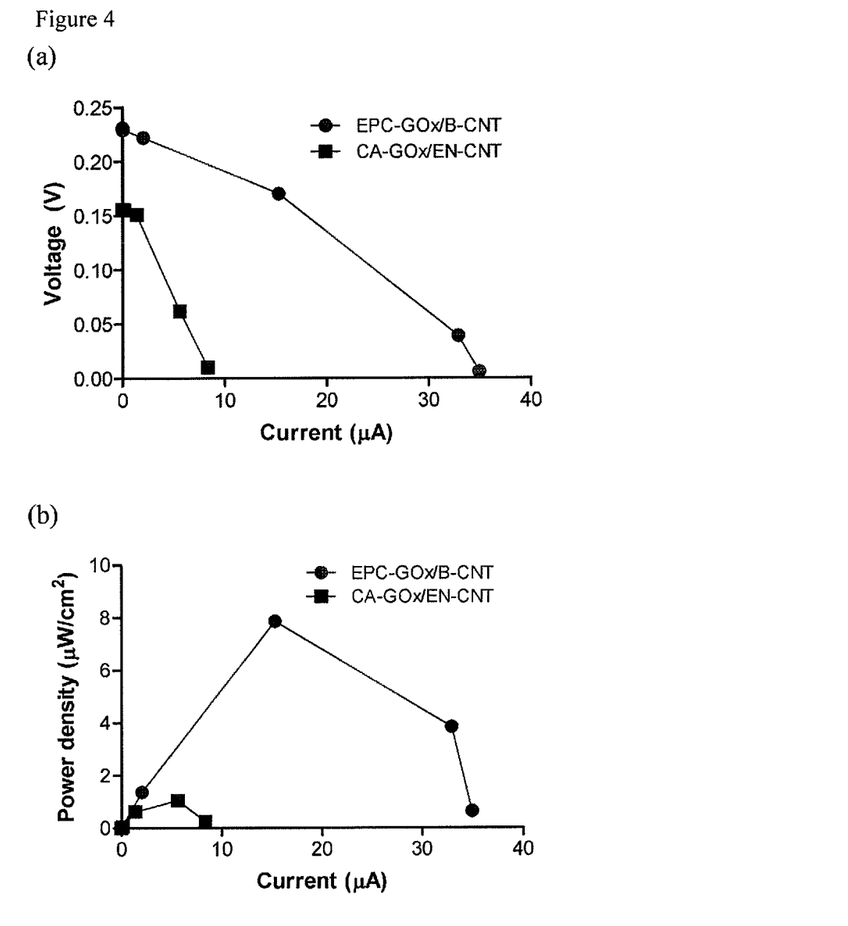

CA-GOx/EDC-NHS-CNTs and EPC-GOx/B-CNTs were used together with carbon papers to prepare respective enzyme electrodes, which were then used to fabricate enzyme-based biofuel cells. The electrochemical performance of the enzyme electrodes was measured using current-voltage characteristic (VI) plots thereof (FIG. 4). According to the VI plots, the biofuel cell employing EPC-GOx/B-CNTs produced higher open cell potential (OCP), lower overpotential and higher maximum power density values than the biofuel cell employing CA-GOx/EDC-NHS-CNTs. The power density graphs were plotted based on the respective VI graphs. The biofuel cell employing EPC-GOx/B-CNTs showed higher power density values in the investigated entire current density range than the biofuel cell employing CA-GOx/EDC-NHS-CNTs. Moreover, the maximum power density of the biofuel cell employing EPC-GOx/B-CNTs was about 7 times higher than that of the biofuel cell employing CA-GOx/EDC-NHS-CNTs. The improved electrochemical performance of the biofuel cell employing EPC-GOx/B-CNTs can be explained by electron generation rate and electron transfer constant.

In the enzyme electrodes, the electron generation rates are proportional to the activity of the enzyme per unit weight of CNTs. As can be seen from FIG. 2, EPC-GOx/B-CNTs showed a higher electron generation rate than CA-GOx/EDC-NHS-CNTs. Since the amounts of the CNTs loaded on the electrodes were fixed in all experiments, the biofuel cell employing EPC-GOx/B-CNTs showed a higher electron generation rate per hour than the biofuel cell employing CA-GOx/EDC-NHS-CNTs. However, electrons produced in the enzyme electrodes should be collected at the current collectors for electrochemical performance measurement. Electron transfer constants in the final portions can be used to prove how effectively the respective enzyme electrodes can collect electrons from the active sites of the enzyme. The electron transfer constant of EPC-GOx/B-CNTs was much higher than that of CA-GOx/EDC-NHS-CNTs. These results reveal that EPC-GOx/B-CNTs produced a larger number of electrons per unit weight of CNTs and more efficiently transferred the electrons than CA-GOx/EDC-NHS-CNTs. In conclusion, EPC-GOx/B-CNTs showed better electrochemical performance than CA-GOx/EDC-NHS-CNTs.

It may be controversial that the higher loading of the enzyme is simply responsible for the better electrochemical performance of EPC-GOx/B-CNTs than that of CA-GOx/EDC-NHS-CNTs. Assuming that this controversy is fact, the OCP values should be similar to each other in the respective enzyme electrodes. Against this assumption, however, the biofuel cell employing EPC-GOx/B-CNTs showed higher OCP values than the biofuel cell employing CA-GOx/EDC-NHS-CNTs. This reveals improved inherent electrical properties of the biofuel cell employing EPC-GOx/B-CNTs. Moreover, the biofuel cell employing EPC-GOx/B-CNTs showed higher maximum power density values than the activity of the enzyme. The different proportions of the maximum power density and the enzyme activity are because of different electron transfer constants thereof. A product of the enzyme activity ratio 4.59 and the transfer constant ratio 1.68 was similar to the maximum power density ratio 7.49 (Table 1). Therefore, the improved electrochemical performance of EPC-GOx/B-CNTs may be thought to be due to the combined results of the high electron generation and the high electron transfer efficiency.

TABLE 1

|  | Activity ($\Delta A_{500} min^{-1} per mgCNTs$) | Maximum Power density ($\mu W\ cm^{-2}$) | Electron transfer rate constant ($s^{-1}$) |
|---|---|---|---|
| CA-GOx/EN-CNT | 0.0074 | 1.05 | 1.831 |
| EPC-GOx/B-CNT | 0.034 | 7.86 | 3.085 |
| Ratio* | 4.59 | 7.49 | 1.68 |

Figure 6A:
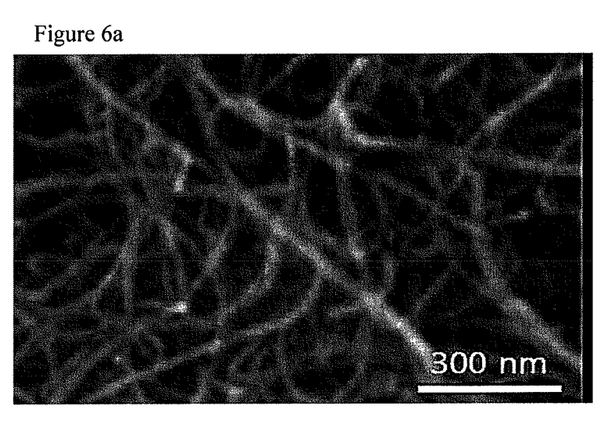
FIG. 6a is a SEM image of B-CNTs whose surface was unmodified.
Figure 6B:
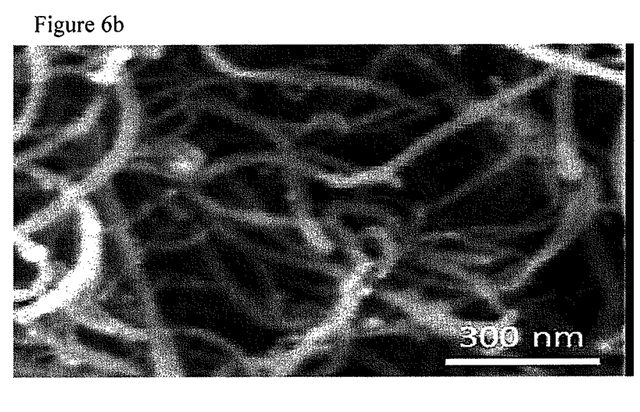
FIG. 6b is a SEM image of CNTs whose surface was modified with a strong acid.
Figure 6C:
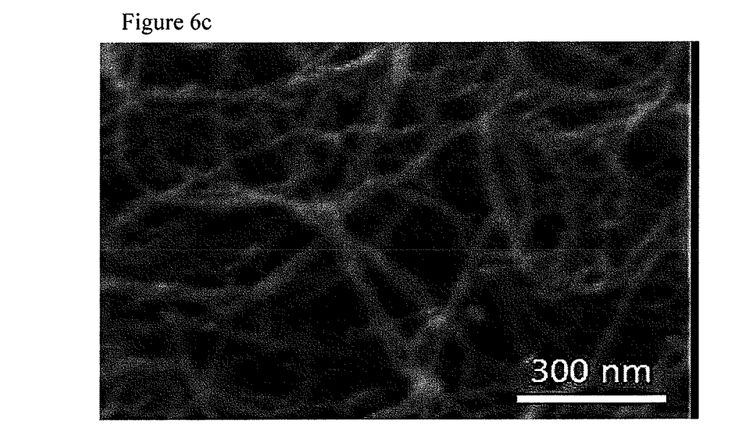
FIG. 6c is a SEM image for CA-GOx/EN-CNTs.
Figure 6D:
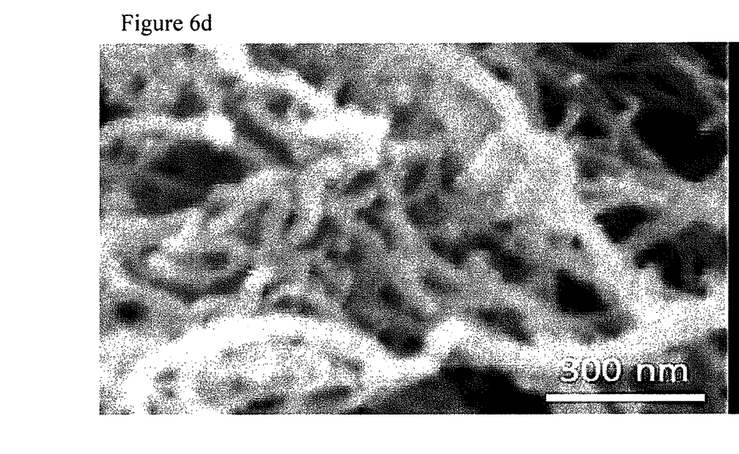
FIG. 6d is a SEM image for EPC-GOx/B-CNTs.

FIG. 6a is a SEM image of the B-CNTs whose surface was unmodified, FIG. 6b is a SEM image of the CNTs whose surface was modified with a strong acid, FIG. 6c is a SEM image for CA-GOx/EN-CNTs, and FIG. 6d is a SEM image for EPC-GOx/B-CNTs. From these SEM images, it can be confirmed that EPC-GOx/B-CNTs includes a significantly large amount of the enzyme immobilized on the surface of the CNTs as compared to CA-GOx/EN-CNTs.

Figure 7A:
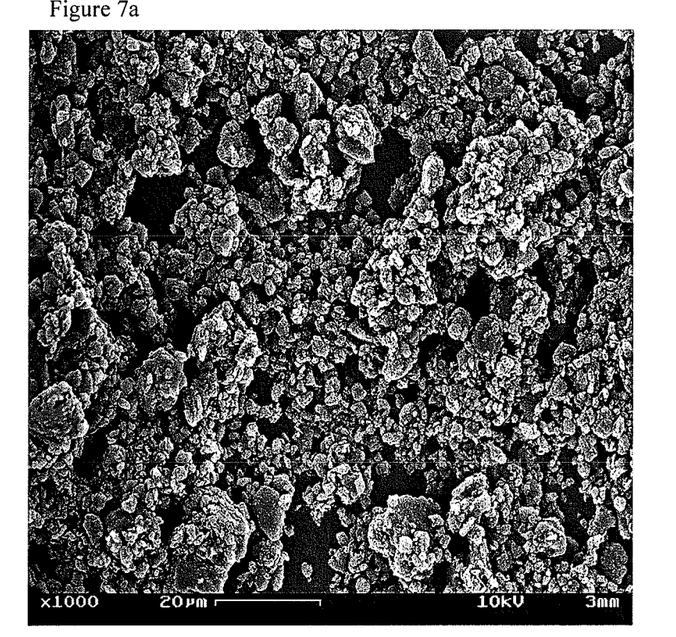
FIGS. 7a and 7b are SEM images of EPC-GOx/B-CNTs taken at magnifications of 1,000× and 120,000×, respectively.
Figure 7B:
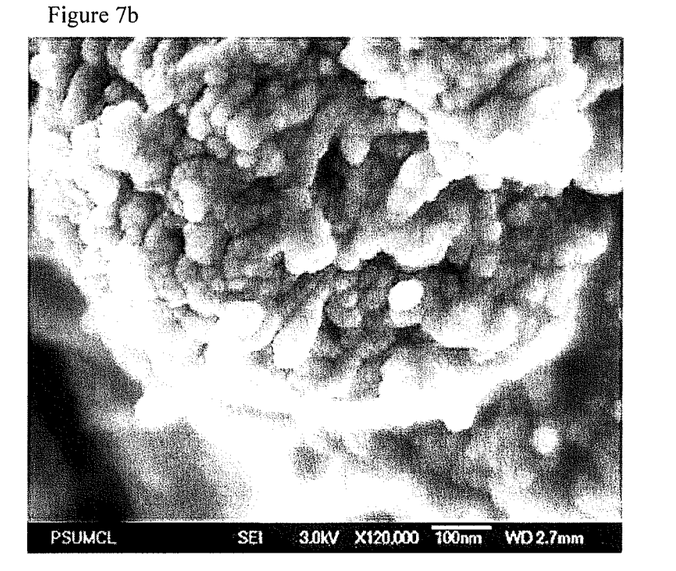

FIGS. 7a and 7b are SEM images of EPC-GOx/B-CNTs taken at magnifications of 1,000× and 120,000×, respectively. The images show that the GOx formed shells around the B-CNTs and the shells were much thicker than shells of the composites produced by the other methods, demonstrating the immobilization of a large amount of the enzyme in EPC-GOx/B-CNTs.

INDUSTRIAL APPLICABILITY

The use of the composite of enzyme and carbon structure according to the present invention enables the fabrication of biosensors, biofuel cells, enzyme columns, ELISA kits, bioremediation devices, antifouling agents, and ibuprofen production with markedly improved performance as compared to the use of conventional enzyme/carbon structure composites.

The invention claimed is:
1. A method for producing a composite of enzyme and carbon structure, comprising:
(1) dispersing elongated carbon structures in an aqueous enzyme-solution comprising an enzyme so that the enzyme molecules adsorb on a surface of the carbon structures, wherein the surface of the carbon structures is not modified to form functional groups capable of forming covalent bonds with the enzyme molecules;
(2) adding a precipitant to the enzyme solution to cause the enzyme molecules to precipitate and to deposit on the carbon structure; and

(3) adding a cross-linker to cross-link the precipitated enzyme molecules, wherein the cross-linked enzyme molecules surround the carbon structures, and wherein there is no covalent bonding between the carbon structures and the enzyme molecules.

2. The method according to claim 1, wherein the carbon structures have a diameter in a micrometer or nanometer range.

3. The method according to claim 2, wherein the carbon structures are selected from carbon tubes, carbon rods, and carbon wires.

4. The method according to claim 1, wherein electron conductivity of the carbon structures is preserved.

5. The method according to claim 1, wherein the precipitant is selected from aqueous solutions of methanol, ethanol, 1-propanol, 2-propanol, butyl alcohol, acetone, PEG, ammonium sulfate, sodium chloride, sodium sulfate, sodium phosphate, potassium chloride, potassium sulfate and potassium phosphate, and mixtures thereof.

6. The method according to claim 1, wherein the precipitant has a concentration of 10 to 50% by weight.

7. The method according to claim 1, wherein the cross-linker comprises one or more compounds selected from the group consisting of diisocyanates, dianhydrides, diepoxides, dialdehydes, diimides, 1-ethyl-3-dimethylaminopropylcarbodiimide, glutaraldehyde, bis(imido esters), bis(succinimidyl ester), and diacid chlorides.

8. The method according to claim 1, wherein the enzyme molecules form shells surrounding the carbon structures without the formation of covalent bonds between the enzyme and the carbon structures.

9. The method according to claim 1, wherein the enzyme is selected from the group consisting of chymotrypsin, trypsin, subtilisin, papain, lipase, horse radish peroxidase, soybean peroxidase, chloroperoxidase, manganese peroxidase, tyrosinase, laccase, cellulase, xylanase, lactase, sucrase, organophosphohydrolase, cholin esterase, glucose oxidase, alcohol dehydrogenase, glucose dehydrogenase, hydrogenase, glucose isomerase, and mixtures thereof.

10. A composite of enzyme and carbon structure comprising:
   elongated carbon structures, wherein a surface of the carbon structures is not modified to introduce functional groups capable of forming covalent bonds with enzyme molecules; and
   one or more shells comprising crosslinked enzyme molecules surrounding the carbon structures,
   wherein there is no covalent bonding between the enzyme molecules and the carbon structures.

11. The composite according to claim 10, wherein the carbon structures are selected from carbon nanotubes, carbon nanorods, and carbon nanowires.

12. The composite according to claim 10, wherein electron conductivity of the carbon structures is preserved.

13. The composite according to claim 10, wherein each of the one or more shells has a thickness of 10 to 1,000 nm.

14. A device selected from the group consisting of biosensors, biofuel cells, enzyme columns, ELISA kits, bioremediation devices, antifouling agents, and ibuprofen production, wherein the device comprises the composite according to claim 10.

* * * * *